United States Patent [19]
Hargrave et al.

[11] Patent Number: 5,593,979
[45] Date of Patent: Jan. 14, 1997

[54] PYRIDOBENZO-AND PYRIDIOTHIENO-DIAZEPINES USEFUL FOR THE TREATMENT OF HIV INFECTION

[75] Inventors: Karl D. Hargrave, Brookfield; Ernest Cullen; John R. Proudfoot, both of Newtown; Karl G. Grozinger, Ridgefield; Kollol Pal, New Milford; Julian Adams, Ridgefield, all of Conn.

[73] Assignee: Boehringer Ingelheim Pharmaceuticals, Inc., Ridgefield, Conn.

[21] Appl. No.: 366,131

[22] Filed: Dec. 29, 1994

Related U.S. Application Data

[63] Continuation of Ser. No. 239,634, May 9, 1994, abandoned, which is a continuation of Ser. No. 95,779, Jul. 21, 1993, abandoned, which is a continuation of Ser. No. 966,993, Oct. 27, 1992, abandoned, which is a continuation of Ser. No. 837,714, Feb. 19, 1992, abandoned, which is a continuation of Ser. No. 652,157, Feb. 7, 1991, abandoned.

[51] Int. Cl.$^6$ .......... A61K 31/55; C07D 471/04; C07D 495/14
[52] U.S. Cl. .......... 514/81; 514/220; 540/542; 540/557
[58] Field of Search .......... 540/542, 557; 514/81, 220

[56] References Cited

U.S. PATENT DOCUMENTS 5,087,625  2/1992  Hargrave et al. .......... 514/220

OTHER PUBLICATIONS

J. Benditt and J. Cohen, *Science*, vol. 260, May 28, 1993, pp. 1253–1255.
Sandstrom et al., Review Article in *Drugs*, 34, pp. 373–390 (1987).
Yarchoan et al, *AIDS: Modern Concepts And Therapeutic Challanges*, Marcel Dekker Inc., pp. 335–360 (1987).
Hahn et al, "Nucleotide Dimers as Anti–Human Immuno-–deficiency Virus Agents," in Nucleotide Analogues (1989).
Antiviral Agents, Martin ed., Amer. Chem. Soc., pp. 156–159, Mar., *Advanced Organic Chem.*, 3rd ed (1985), pp. 527–529.

*Primary Examiner*—Philip I. Datlow
*Attorney, Agent, or Firm*—Robert P. Raymond; Alan R. Stempel; Mary-Ellen M. Devlin

[57] ABSTRACT

Disclosed are novel pyrido[2,3-b][1,4]benzodiazepines. These compounds are useful in the treatment of AIDS, ARC and related disorders associated with HIV infection. The compounds are of the class having the structure:

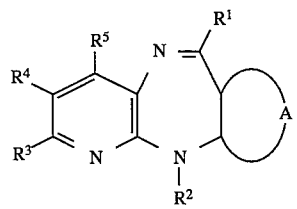

4 Claims, No Drawings

PYRIDOBENZO- AND PYRIDIOTHIENO-DIAZEPINES USEFUL FOR THE TREATMENT OF HIV INFECTION

This is a continuation of application Ser. No. 239,634, filed May 9, 1994, abandoned which is a continuation of application Ser. No. 095,779, filed Jul. 21, 1993, now abandoned, which is a continuation of application Ser. No. 966,993, filed Oct. 27, 1992, now abandoned, which is a continuation of application Ser. No. 837,714, filed Feb. 19, 1992, now abandoned, which is a continuation of application Ser. No. 652,157, Feb. 7, 1991, now abandoned.

FIELD OF THE INVENTION

The invention relates to novel pyridobenzo-and pyridothieno-diazepines, methods for preparing these compounds, the use of these and related but known compounds in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins.

The conversion of the RNA to DNA is accomplished through the use of the enzyme reverse transcriptase (RT), which is included within the infecting vision along with the RNA. Reverse transcriptase has three enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Next, acting as a ribonuclease, RT frees the DNA just produced from the original vital RNA and then destroys the original RNA. Finally, acting as a DNA-dependent DNA polymerase, RT makes a second, complementary, DNA strand, using the first DNA strand as a template. The two strands form double-stranded DNA, the form of DNA found in the host cell's genome, which is integrated into the host cell's genome by another enzyme, called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

SUMMARY OF THE INVENTION

A first aspect of the invention comprises novel pyrido[2,3-b][1,4]benzodiazepines. A second aspect of the invention comprises a method for preventing or treating HIV-1 infection which comprises administering, to a human exposed to or infected by HIV-1, a prophylactically or therapeutically effective amount of these novel pyrido[2,3-b][1,4]benzodiazepines. A third aspect of the invention comprises methods for making these novel compounds. A final aspect of the invention comprises pharmaceutical compositions suitable for the prevention or treatment of HIV-1 infection comprising the above mentioned compounds.

DETAILED DESCRIPTION OF THE INVENTION

A first aspect of the invention comprises novel pyridodiazepines of the formula I

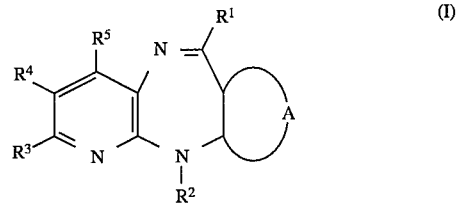

wherein,
A is a fused ring of the formula

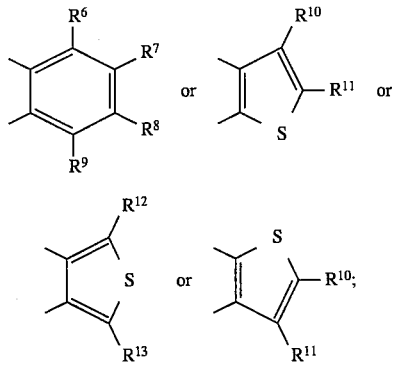

$R^1$ is cyano, chloro, bromo, imidazolyl, phosphentanyl, phospholanyl, or phosphorinanyl, or a group of the formula $—OR^{14}$, $—SR^{14}$, $—SOR^{14}$, $—SO_2R^{14}$, $—NH_2$, $NHR^{14}$, $—NR^{14}R^{15}$, $—PR^{14}R^{15}$, $—P(OR^{14})(OR^{15})$, $—P(O)(OR^{14})(OR^{15})$, $—PO_3H_2$, $—P(NR^{14}R^{15})(NR^{14}R^{15})$, or $—P(O)(NR^{14}R^{15})(NR^{14}R^{15})$, wherein $R^{14}$ and $R^{15}$ are each independently alkyl of 4 carbon atoms, which may optionally be substituted by a cyano or alkoxycarbonyl group of 2 to 4 carbon atoms, cyclopropyl or cyclobutyl, or the group $—NR^{14}R^{15}$ may be pyrrolidine, piperidine, or morpholine;

$R^2$ is alkyl or fluoroalkyl of 1 to 4 carbon atoms, cycloalkyl of 3 to 5 carbon atoms, alkenyl or alkynyl of 2 to 4 carbon atoms, alkoxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl, thienyl or furanyl, which is either unsubstituted or substituted by alkyl or alkoxy of 1 to 3 carbon atoms, hydroxyl or halogen), phenyl (which is either unsubstituted or substituted by alkyl or alkoxy of 1 to 3 carbon atoms, halogen or hydroxyl) or alkoxycarbonylmethyl wherein the alkoxy moiety contains 1 to 5 carbon atoms;

$R^3$, $R^4$ and $R^5$ are each independently hydrogen, alkyl of 1 to 3 carbon atoms or chloro, with the proviso that at least one of these substituents is hydrogen or methyl; or, one of $R^3$, $R^4$ and $R^5$ is butyl, alkanoyl of 2 to 4 carbon atoms, alkoxycarbonyl or 2 to 4carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, aryl or arylalkyl (wherein the alkyl moiety contains 1 to 3 carbon atoms, and the aryl moiety is phenyl, thienyl, furanyl, pyridyl, or imidazolyl, which is either unsubstituted or substituted by alkyl or alkoxy of 1 to 3 carbon atoms, hydroxyl or halogen), alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 3 carbon atoms, N-pyrrolidino, N-piperidino, N-morpholino, carboxyalkyl of 2 to 3 carbon atoms, cyano, nitro, carboxyl, carbamyl, amino, azido, mono- or di-alkylaminoalkyl wherein each alkyl moiety contains 1 to 2 carbon atoms, with the proviso that the remaining two substituents are hydrogen or methyl;

$R^6$, $R^7$, $R^8$ and $R^9$ are each hydrogen; or one of $R^6$, $R^7$, $R^8$ and $R^9$ is alkyl of 1 to 4 carbon atoms, alkanoyl of 2 to 4 carbon atoms alkoxycarbonyl of 2 to 4 carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 2 carbon atoms, carboxyalkyl of 2 to 3 carbon atoms, cyano, nitro, carboxyl, carbamyl, amino, azido, mono- or dialkylaminoalkyl wherein each alkyl moiety contains 1 to 2 carbon atoms, and the remaining three substituents are hydrogen or two of the remaining three substituents are hydrogen and one is methyl, ethyl or halogen;

$R^{10}$ and $R^{11}$ are each independently hydrogen, alkyl of 1 to 3 carbon atoms or halogen; and, $R^{12}$ and $R^{13}$ are each independently hydrogen, methyl, ethyl, or halogen.

In a subgeneric aspect, the invention comprises compounds of the formula Ia,

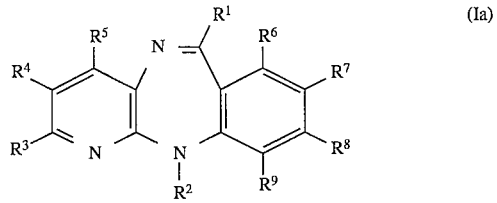

wherein, $R^1$ is cyano, chloro, imidazolyl, or a group of the formula —$OR^{14}$, —$SR^{14}$, —$SOR^{14}$, —$SO_2R^{14}$, —$NH_2$, —$NHR^{14}$, or —$NR^{14}R^{15}$, wherein $R^{14}$ and $R^{15}$ are each independently alkyl of 4 carbon atoms, which may optionally be substituted by a cyano or alkoxycarbonyl group of 2 to 4 carbon atoms, cyclopropyl or cyclobutyl, or the group —$NR^{14}R^{15}$ may be pyrrolidine, piperidine, or morpholine;

$R^2$ is alkyl 1 to 4 carbon atoms, cycloalkyl of 3 to 4 carbon atoms, alkenyl or alkynyl of 2 to 4 carbon atoms, alkoxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy or halogen) or alkoxycarbonylmethyl wherein the alkoxy moiety contains 1 to 4 carbon atoms;

$R^3$, $R^4$, and $R^5$ are each independently hydrogen, methyl, chloro, mono- or di-alkylamino wherein each alkyl moiety contains 1 to 3 carbon atoms, N-pyrrolidino, N-piperidino or N-morpholino, with the proviso that at least one of these substituents is hydrogen or methyl, or $R^5$ is ethyl, propyl or butyl with the remaining two substituents being hydrogen;

$R^6$ is hydrogen, or methyl or ethyl with the proviso that $R^7$ is hydrogen or methyl;

$R^7$ is alkyl of 1 to 2 carbon atoms, acetyl, hydroxyalkyl of 1 to 2 carbon atoms, alkoxycarbonyl of 2 to 3 carbon atoms, alkoxycarbonylalkyl wherein the alkoxy and alkyl moieties each contain 1 to 2 carbon atoms, halogen, trifluoromethyl, hydroxyl, alkoxy of 1 to 2 carbon atoms, alkylthio of 1 to 2 carbon atoms, acetyloxy, alkanoylamino of 1 to 2 carbon atoms or cyano, with the proviso that $R^8$ is hydrogen;

$R^8$ is alkyl of 1 to 2 carbon atoms, acetyl, hydroxyalkyl of 1 to 2 carbon atoms, alkoxycarbonyl of 2 to 3 carbon atoms, alkoxycarbonylalkyl wherein the alkoxy and alkyl moieties each contain 1 to 2 carbon atoms, halogen, trifluoromethyl, hydroxyl, alkoxy of 1 to 2 carbon atoms, alkylthio of 1 to 2 carbon atoms, acetyl, alkanoylamino of 1 to 2 carbon atoms or cyano, with the proviso that $R^7$ is hydrogen; or, $R^7$ and $R^a$ are both hydrogen, methyl or halogen; and, $R^9$ is hydrogen or methyl with the proviso that $R^8$ is hydrogen or methyl.

In a further subgeneric aspect, the invention comprises compounds of the formula Ia, wherein, $R^1$ is cyano, chloro, imidazolyl, or a group of the formula —$OR^{14}$, —$SR^{14}$, —$SOR^{14}$, —$SO_2R^{14}$, —$NH_2$, —$NHR^{14}$, or —$NR^{14}R^{15}$, wherein $R^{14}$ and $R^{15}$ are each independently alkyl of 4 carbon atoms, which may optionally be substituted by a cyano or alkoxycarbonyl group of 2 to 4 carbon atoms, cyclopropyl or cyclobutyl, or the group —$NR^{14}R^{15}$ may be pyrrolidine, piperidine, or morpholine;

$R^2$ is alkyl of 1 to 4 carbon atoms or cycloalkyl of 3 to 4 carbon atoms;

$R^3$ is hydrogen, methyl, chloro, methoxy, mono- or di-alkylamino wherein each alkyl moiety contains 1 to 3 carbon atoms, or N-pyrrolidino;

$R^4$ and $R^5$ are each independently hydrogen or methyl; and, $R^6$ through $R^9$ are each hydrogen.

SYNTHESIS OF COMPOUNDS OF FORMULA I AND THEIR SALTS

The compounds of Formula I and their salts can be prepared by known methods or obvious modifications thereof. Methods A–I, described below, are illustrative of the methods for preparing the compounds.

Method A (nitrile)

Compounds of the formula I, wherein $R^2$ through $R^{13}$ are as defined above and $R^1$ is cyano, can be obtained by treating a trifluoromethanesulfonate of formula I, wherein $R^2$ through $R^{13}$ are as defined above and $R^1$ is trifluoromethanesulfonate, with cyanide ion. Convenient sources of cyanide ion include, for example, tetraethylammonium cyanide, diethylaluminum cyanide, potassium cyanide, or sodium cyanide. The reaction is preferably carded out in an inert solvent, for example, methylene chloride, chloroform, dimethylformamide, dimethylsulfoxide, diethylether, or tetrahydrofuran, at a temperature between 0° C. and the boiling point of the reaction mixture.

Method B (halide)

Compounds of the formula I, wherein $R^2$ through $R^{13}$ are as defined above and $R^1$ is chloro or bromo, can be obtained by treating a lactam of the formula II,

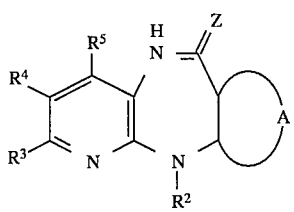

(II)

wherein A and $R^2$ through $R^{13}$ are as defined above and Z is oxygen, with a halogenating agent in an inert solvent Chlorinating agents which may be used include, for example, phosphorus. pentachloride, phosphorus oxychloride, and sulfuryl chloride. Brominating agents which may be used include, for example, phosphorus pentabromide or phosphorus oxybromide. The reaction is conveniently carried out at temperatures of between 0° C. and the boiling point of the reaction mixture, preferably at temperatures above ambient temperature, and inert solvents which may be used include, for example, toluene, xylene, dichloroethane, or trichlorobenzene.

Method C (alkoxide)

Compounds of the formula I, wherein $R^1$ is a group of the formula —$OR^{14}$, and $R^2$ through $R^{14}$ are as defined above, may be obtained by reacting a compound of the formula I, wherein $R^1$ is cyano and $R^2$ through $R^{13}$ are as defined above, with an alcohol of formula $R^{14}OH$. The condensation is conveniently carried out in the presence of a base including, but not limited to, an alkali metal or alkaline earth metal hydroxide, such as lithium hydroxide, barium hydroxide, sodium hydroxide or potassium hydroxide, or an alkali metal alkoxide, such as sodium methoxide or potassium tert-butoxide, and using the alcohol as solvent, at a temperature between –20° C. and +50° C. It is preferable that the alkali metal alkoxide utilized be derived from the alcohol which is used as solvent.

Method D (alkylthio)

Compounds of the formula I, wherein $R^1$ is a group of the formula —$SR^{14}$, and $R^2$ through $R^{14}$ are as defined above, may be obtained by convening a compound of the formula II, wherein $R^2$ through $R^{13}$ are as defined above and Z is sulfur, into the corresponding 5-alkali or alkaline earth metal compound and subsequently reacting the alkali metal compound with a compound of the formula III $$R^{14}X \qquad (III)$$

wherein $R^{14}$ has the same meanings as defined above and X is the radical of a reactive ester, a halogen atom, the group $OSO_2R$, wherein R is methyl, ethyl or an aromatic group.

The conversion of a compound of formula II into the corresponding alkali metal or alkaline earth metal compound may be effected by reacting a compound of formula II with an alkali metal or alkaline earth metal hydroxide, such as lithium hydroxide, barium hydroxide, sodium hydroxide or potassium hydroxide, with an alkali metal alkoxide, such as sodium methoxide or potassium tert-butoxide, with an alkali metal amide, such as sodium amide or potassium amide, or with an alkali metal hydride such as sodium hydride or potassium hydride. The reaction is preferably carried out at temperatures between –78° C. and +50° C., and in the presence of a suitable organic solvent. Inert organic solvents, such as dimethylformamide, dimethylsulfoxide, tetrahydrofuran, glycoldimethyl ether, toluene, pyridine, or methylene chloride are preferred. For conversion of the alkali or alkaline earth metal-substituted compound thus obtained into a compound of general formula I, the solution or suspension of the alkali or alkaline earth metal compound is reacted directly, i.e. without isolation, with a compound of formula III. Substitution takes place at the sulfur atom in the 6-position of the pyridobenzodiazepinone, provided that one equivalent of base and one equivalent of a compound of formula Ill are used.

It will be obvious to those skilled in the art that the presence of nucleophilic substituents in the compounds of formula II may require the use of an intermediate of formula II having substituents which are, other than the 11-position nitrogen, not nucleophilic but which can be derivatized to yield the required group. For example, amino or monoalkylamino substituents at any of $R^3$ through $R^{13}$ may be obtained by alkylating or acylating an intermediate of formula II having a nitro group at any of $R^3$ through $R^{13}$, and subsequently reducing the nitro group, and alkylating, if appropriate, to yield the final product.

Method E (sulfoxide)

Compounds of the formula I, wherein $R^1$ is a group of the formula —$SOR^{14}$, and $R^2$ through $R^{14}$ are as defined above, may be obtained by oxidizing a compound of the formula I, wherein $R^1$ is a group of the formula —$SR^{14}$ and $R^2$ through $R^{14}$ are as defined above. Oxidizing agents which may be used include peroxides such as 30% hydrogen peroxide, peracids such as m-chloroperbenzoic acid or trifluoroperacetic acid, sodium periodate, sodium perborate, or t-butyl hypochlorite. The reaction is carried out in inert solvents such as methylene chloride, dichloroethane, acetic acid, acetone, and toluene at temperatures generally from –78° C. to 25° C.

Method F (sulfone)

Compounds of the formula I, wherein $R^1$ is a group of the formula —$SO_2R^{14}$, and $R^2$ through $R^{14}$ are as defined above, may be obtained by oxidizing a compound of the formula I, wherein $R^1$ is a group of the formula —$SR^{14}$ or —$SOR^{14}$, and $R^2$ through $R^{14}$ are as defined above. Oxidizing agents which may be used include peroxides such as 30% hydrogen peroxide, potassium permanganate, potassium hydrogen persulfate, peracids such as m-chloroperbenzoic acid or trifluoroperacetic acid, sodium periodate, sodium perborate, or t-butyl hypochlorite. The reaction can be carried Out in inert solvents such as methylene chloride, dichloroethane, acetic acid, acetone, and toluene at temperatures generally from –78° C. to 25° C. Generally, these reactions are performed analogous to those for for the preparation of the corresponding sufoxides, except that an additional equivalent of oxidizing agent is utilized, and the reaction may be carried out at higher temperatures.

Method G (amine).

Compounds of formula I, wherein $R^1$ is a group of the formula —$NHR^{14}$, —$NR^{14}R^{15}$, or imidazolyl, and $R^2$ through $R^{15}$ are as defined above, may be obtained by reaction of a compound of formula I, wherein $R^1$ is trifluoromethanesulfonate, with a molar excess of ammonia or an amine of the formula $H_2NR^{14}HNR^{14}R^{15}$, or 1-imidazolyl. The condensation is generally carried out in an inert solvent such as methylene chloride, dioxane, dimethylformamide, dimethylsulfoxide, tetrahydrofuran, or toluene, at temperatures between –20° C. up to the boiling point of the solvent.

Method H (phosphorous compounds)

Compounds of formula I, wherein R' is a group of the formula —$PR^{14}R^{15}$, —$P(OR^{14})(OR^{15})$, —$P(O)(OR^{14})(OR^{15})$, —$P(NR^{14}R^{15})(NR^{14}R^{15})$, —$P(O)(NR^{14}R^{15})(NR^{14}R^{15})$, P-phosphetanyl, P-phospholanyl, or P-phosphorinanyl, and $R^2$ through $R^{15}$ are as defined above, may be obtained by transmetallation of a compound of formula I, wherein $R^1$ is halogen with a bulky alkyl-lithium reagent such as t-butyllithium. The reaction is generally carried out in inert solvents such as tetrahydrofuran, diethyl ether, 1,4-dioxane, and glycoldimethyl ether. The lithio derivative thus formed is then reacted with an appropriate halophosphorous compound of the formula $XPR^{14}R^{15}$, $XP(OR^{14})(OR^{15})$, $XP(O)(OR^{14})(OR^{15})$, $XP(NR^{14}R^{15})(NR^{14}R^{15})$, $XP(O)(NR^{14}R^{15})(NR^{14}R^{15})$, P-halophosphetanyl, P-halophospholanyl, or P-halophosphofinanyl, wherein X is halogen. These reactions are generally carried out in a single reaction vessel at temperatures between −78° C. and room temperature.

Method I (phosphonic acids)

Compounds of formula I, wherein $R^1$ is a group of the formula —$PO_3H_2$ and $R^2$ through $R^{13}$ are as defined above, may be obtained by hydrolysis of a compound of formula I, wherein $R^1$ is a group of formula —$P(OR^{14})(OR^{15})$, wherein $R^2$ through $R^{15}$ are as defined above. The hydrolysis is generally carried out in an aqueous solution containing an alkaline earth metal hydroxide, such as lithium hydroxide, barium hydroxide, sodium hydroxide or potassium hydroxide, optionally in the presence of an inert organic solvent such as methanol or ethanol, at temperatures between 0° C. and the boiling point of the reaction mixture.

Starting Materials for Methods A through I

The preparation of compounds of formula I wherein $R^1$ is trifluoromethanesulfonate and $R^2$ through $R^{13}$ are as defined above, and compounds of formula II wherein $R^2$ through $R^{13}$ are as defined above, can be obtained by procedures described in copending U.S. patent application Ser. No. 650,141 now issued as U.S. Pat. No. 5,087,625 filed Feb. 4, 1991.

Those skilled in the an will realize that it will at times be more convenient to make certain compounds of formula I by derivatization of other compounds of formula I, rather than by making them directly, using one of the above-described Methods A–G. Such derivatizations will employ known reaction techniques. As non-limiting examples, a nitro group can be reduced to yield an amine; a methoxy group can convened to hydroxy by standard demethylation procedures and hydroxy can, in appropriate settings, be in turn replaced with amine via the trifluoromethanesulfonyloxy derivative; an amine can be acylated to yield an alkanoylamine or can be alkylated to yield the mono- or dialkylamine; a halogen can be replaced, in appropriate settings, by an amine; and a protecting group can be removed.

Formation of Salts and Other Derivatives

Compounds of formula I may, if desired, be convened into their non-toxic, pharmaceutically acceptable addition salts by conventional methods; for example, by dissolving a compound of formula I in a suitable solvent and treating the solution with one or more molar equivalents of the desired acid or base, as appropriate. The invention-also comprises such salts.

Examples of inorganic and organic acids which may form nontoxic, pharmaceutically acceptable acid addition salts with a compound of the formula I are the following: hydrochloric acid, hydrobromic acid, sulfuric acid, phosphoric acid, nitric acid, methanesulfonic acid, tartaric acid, fumaric acid, acetic acid, and the like. Examples of inorganic and organic bases which may form nontoxic, pharmaceutically acceptable basic addition salts with a compound of the formula I are the following: Sodium hydroxide, potassium hydroxide, magnesium hydroxide, ammonia. tromethamine, and the like. Compounds of formula I may form addition salts with one molar equivalent of the acid or base, as appropriate.

Biological Properties

The above-described compounds of Formula I, and their salts, possess inhibitory activity against HIV-1 reverse transcriptase. When administered in suitable dosage forms, they are useful in the prevention or treatment of AIDS, ARC and related disorders associated with HIV infection. Another aspect of the invention, therefore, is a method for preventing or treating HIV-1 infection which comprises administering to a human being, exposed to or infected by HIV-1, a prophylactically or therapeutically effective amount of a novel compound of Formula I or Ia, as described above.

The compounds formula I may be administered in single or divided doses by the oral, parenteral or topical routes. A suitable oral dosage for such compounds would be in the range of about 5 to 1000 mg per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When such compounds are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkyleneglycols, petroleum jelly and the like. The pharmaceutical preparations can be prepared in a conventional manner and finished dosage forms can be solid dosage forms, for example, tablets, dragees, capsules, and the like, or liquid dosage forms, for example, solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers, such as polyethylene glycol.

For parenteral use, it is preferred to administer such compounds in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds can also be administered as solutions for nasal applications which may contain, in addition to the compounds, suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinyl-pyrrolidone, polysorbates or glycerin. Microbial preservatives added may include benzalkonium chloride, thimerosal, chlorobutanol or phenylethyl alcohol.

Additionally, such compounds can be administered by suppository.

The following examples are intended to further illustrate the invention.

EXAMPLE A

Capsules or Tablets

| A-1 | | A-2 | |
|---|---|---|---|
| Ingredients | Quantity | Ingredients | Quantity |
| Compound | 250 mg | Compound | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound is blended into a powder mixture with the premixed excipient materials as identified above with the exception of the lubricant. The lubricant is then blended in and the resulting blend compressed into tablets or filled into hard gelatin capsules.

EXAMPLE B

Parenteral Solutions

| Ingredients | Quantity |
|---|---|
| Compound | 500 mg |
| Tartaric acid | 1.5 g |
| Benzyl Alcohol | 0.1% by weight |
| Water for injection | q.s. to 100 ml |

The excipient materials are mixed with the water and thereafter the compound is added. Mixing is continued until the solution is clear. The pH of this solution is adjusted to 3.0 and is then filtered into the appropriate vials or ampoules and sterilized by autoclaving.

EXAMPLE C

Nasal Solutions

| Ingredients | Quantity |
|---|---|
| Compound | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 ml |

The excipient materials are mixed with the water and thereafter the compound is added and mixing is continued until the solution is clear. The pH of this solution is adjusted to 4.0 and is then filtered into the appropriate vials or ampoules.

We claim:

1. A compound of the formula I

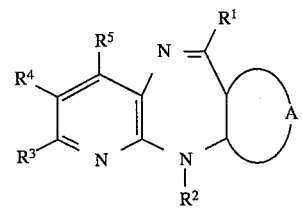

wherein,

A is a fused ring of the formula

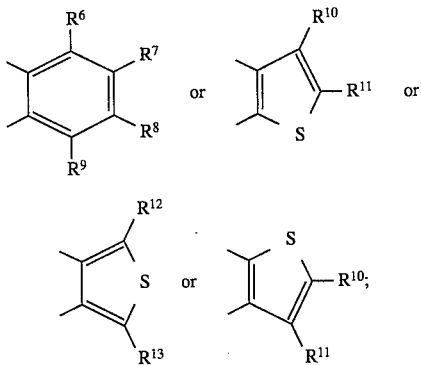

$R^1$ is cyano, chloro, bromo, imidazolyl, phosphetanyl, phospholanyl, or phosphorinanyl, or a group of the formula $-OR^{14}$, $-SR^{14}$, $-SOR^{14}$, $-SO_2R^{14}$, $-NH_2$, $-NHR^{14}$, $-NR^{14}R^{15}$, $-PR^{14}R^{15}$, $-P(OR^{14})(OR^{15})$, $-P(O)(OR^{14})(OR^{15})$, $-PO_3H_2$, $-P(NR^{14}R^{15})(NR^{14}R^{15})$, or $-P(O)(NR^{14}R^{15})(NR^{14}R^{15})$, wherein $R^{14}$ and $R^{15}$ are each independently alkyl of 4 carbon atoms, which may optionally be substituted by a cyano or alkoxycarbonyl group of 2 to 4 carbon atoms, cyclopropyl or cyclobutyl, or the group $-NR^{14}R^{15}$ may be pyrrolidine, piperidine, or morpholine;

$R^2$ is alkyl or fluoroalkyl of 1 to 4 carbon atoms, cycloalkyl of 3 to 5 carbon atoms, alkenyl or alkynyl of 2 to 4 carbon atoms, alkoxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl, thienyl or furanyl, which is either unsubstituted or substituted by alkyl or alkoxy of 1 to 3 carbon atoms, hydroxyl or halogen), phenyl (which is either unsubstituted or substituted by alkyl or alkoxy of 1 to 3 carbon atoms, halogen or hydroxyl) or alkoxycarbonylmethyl wherein the alkoxy moiety contains 1 to 5 carbon atoms;

$R^3$, $R^4$ and $R^5$ are each independently hydrogen, alkyl of 1 to 3 carbon atoms or chloro, with the proviso that at least one of these substituents is hydrogen or methyl; or, one of $R^3$, $R^4$ and $R^5$ is butyl, alkanoyl of 2 to 4 carbon atoms, alkoxycarbonyl or 2 to 4 carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, aryl or arylalkyl (wherein the alkyl moiety contains 1 to 3 carbon atoms, and the aryl moiety is phenyl, thienyl, furanyl, pyridyl, or imidazolyl, which is either unsubstituted or substituted by alkyl or alkoxy of 1 to 3 carbon atoms, hydroxyl or halogen), alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 3 carbon atoms, N-pyrrolidino, N-piperidino, N-morpholino, carboxyalkyl of 2 to 3 carbon atoms, cyano, nitro, carboxyl, carbamyl, amino, azido, mono- or di-alkylaminoalkyl wherein each alkyl moiety contains 1 to 2 carbon atoms, with the proviso that the remaining two substituents are hydrogen or methyl;

$R^6$, $R^7$, $R^8$ and $R^9$ are each hydrogen; or one of $R^6$, $R^7$, $R^8$ and $R^9$ is alkyl of 1 to 4 carbon atoms, alkanoyl of 2 to 4 carbon atoms, alkoxycarbonyl of 2 to 4 carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 2 carbon atoms, carboxyalkyl of 2 to 3 carbon atoms, cyano, nitro, carboxyl, carbamyl, amino, azido, mono- or di-alkylaminoalkyl wherein each alkyl moiety contains 1 to 2 carbon atoms, and the remaining three substituents are hydrogen or two of the remaining three substituents are hydrogen and one is methyl, ethyl or halogen;

$R^{10}$ and $R^{11}$ are each independently hydrogen, alkyl of 1 to 3 carbon atoms or halogen; and, $R^{12}$ and $R^{13}$ are each independently hydrogen, methyl, ethyl, or halogen;

or a pharmaceutically acceptable addition salt thereof.

2. A compound of the formula Ia

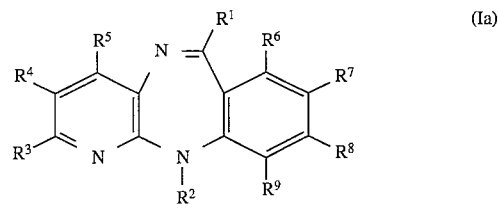

wherein, $R^1$ is cyano, chloro, imidazolyl, or a group of the formula —$OR^{14}$, —$SR^{14}$, —$SOR^{14}$, —$SO_2R^{14}$, —$NH_2$, —$NHR^{14}$, or —$NR^{14}R^{15}$, wherein $R^{14}$ and $R^{15}$ are each independently alkyl of 4 carbon atoms, which may optionally be substituted by a cyano or alkoxycarbonyl group of 2 to 4 carbon atoms, cyclopropyl or cyclobutyl, or the group —$NR^{14}R^{15}$ may be pyrrolidine, piperidine, or morpholine;

$R^2$ is alkyl of 1 to 4 carbon atoms or cycloalkyl of 3 to 4 carbon atoms;

$R^3$ is hydrogen, methyl, chloro, methoxy, mono- or di-alkylamino wherein each alkyl moiety contains 1 to 3 carbon atoms, or N-pyrrolidino;

$R^4$ and $R^5$ are each independently hydrogen or methyl; and, $R^6$ through $R^9$ are each hydrogen;

or a pharmaceutically acceptable addition salt thereof.

3. A method for treating infection by HIV-1 which comprises administering to a human exposed to or infected by HIV-1 a therapeutically effective amount of a compound according to claims 1 or 2.

4. A pharmaceutical composition suitable for the treatment of HIV-1 infection comprising a therapeutically effective amount of a compound according to claims 1 or 2 and a pharmaceutically acceptable carrier.

* * * * *